(12) United States Patent
Hyatt et al.

(10) Patent No.: US 11,840,591 B2
(45) Date of Patent: Dec. 12, 2023

(54) IN SITU PEELABLE PROTECTIVE BARRIER FILMS

(71) Applicant: Sanipeel, LLC, Cleveland, OH (US)

(72) Inventors: Jeremy Hyatt, Revere, MA (US); Rebecca Bader, Oceanside, CA (US)

(73) Assignee: Sanipeel, LLC, Cleveland, OH (US)

( * ) Notice: Subject to any disclaimer, the term of this patent is extended or adjusted under 35 U.S.C. 154(b) by 337 days.

(21) Appl. No.: 17/139,415

(22) Filed: Dec. 31, 2020

(65) Prior Publication Data

US 2022/0204668 A1 Jun. 30, 2022

(51) Int. Cl.
| | | |
|---|---|---|
| C08F 220/18 | (2006.01) | |
| C08F 218/08 | (2006.01) | |
| C08F 220/14 | (2006.01) | |
| C08J 3/07 | (2006.01) | |
| C08J 5/18 | (2006.01) | |
| C08K 5/00 | (2006.01) | |
| C08K 5/138 | (2006.01) | |
| C08K 5/13 | (2006.01) | |

(52) U.S. Cl.
CPC ...... *C08F 220/1804* (2020.02); *C08F 218/08* (2013.01); *C08F 220/14* (2013.01); *C08J 3/07* (2013.01); *C08J 5/18* (2013.01); *C08K 5/0058* (2013.01); *C08K 5/13* (2013.01); *C08K 5/138* (2013.01); *C08F 2800/20* (2013.01); *C08J 2331/04* (2013.01); *C08J 2335/02* (2013.01)

(58) Field of Classification Search
None
See application file for complete search history.

(56) References Cited

U.S. PATENT DOCUMENTS

| | | | |
|---|---|---|---|
| 3,935,137 A | * | 1/1976 | Minkoff ............... C09D 131/04 524/217 |
| 4,654,238 A | | 3/1987 | Yamazaki et al. |
| 5,202,375 A | | 4/1993 | Biale |
| 5,380,785 A | | 1/1995 | Ngoc et al. |
| 5,895,801 A | | 4/1999 | Lee |
| 6,376,094 B1 | | 4/2002 | Dames et al. |
| 6,489,387 B2 | | 12/2002 | Mallya et al. |
| 8,029,704 B2 | | 10/2011 | Dimanshteyn et al. |
| 9,273,236 B2 | | 3/2016 | Gerst et al. |
| 9,421,736 B2 | | 8/2016 | Tobing et al. |
| 9,422,465 B2 | | 8/2016 | Mueller et al. |
| 9,777,166 B2 | | 10/2017 | Lau et al. |

(Continued)

FOREIGN PATENT DOCUMENTS

| | | |
|---|---|---|
| CN | 101230220 A | 7/2008 |
| CN | 101565484 B | 10/2009 |

(Continued)

OTHER PUBLICATIONS

CN-101565484-B, May 2011, Machine translation (Year: 2011).*

(Continued)

*Primary Examiner* — Satya B Sastri
(74) *Attorney, Agent, or Firm* — Dominic A. Frisina (57) ABSTRACT

A water emulsion and film are provided comprising a polyacrylate random copolymer synthesized from acrylic acid (AA), butyl acrylate (BA), methyl methacrylate (MMA), and 2-ethylhexyl acrylate (EHA). The emulsion may be applied to a surface in liquid form, quickly drying to yield a peelable protective barrier film.

11 Claims, 4 Drawing Sheets

(56) References Cited

U.S. PATENT DOCUMENTS

| | | | |
|---|---|---|---|
| 9,914,858 B2 | 3/2018 | Bartholomew et al. | |
| 2003/0073778 A1* | 4/2003 | Zhang | C09D 151/003 |
| | | | 524/556 |
| 2006/0211820 A1* | 9/2006 | Jonn | C08K 5/01 |
| | | | 526/279 |
| 2006/0241229 A1* | 10/2006 | Yoshimura | D06M 15/263 |
| | | | 524/416 |
| 2008/0269402 A1* | 10/2008 | Maurice | C08F 220/14 |
| | | | 524/547 |
| 2013/0048240 A1 | 2/2013 | Hayes | |
| 2018/0221535 A1 | 8/2018 | Burks et al. | |

FOREIGN PATENT DOCUMENTS

| | | | | |
|---|---|---|---|---|
| CN | 101565484 B * | 5/2011 | | |
| CN | 109081889 A | 12/2018 | | |
| EP | 1028151 B1 | 8/2000 | | |
| EP | 1083207 A2 * | 3/2001 | ............... | C08K 3/22 |
| KR | 101012140 B1 | 2/2011 | | |
| WO | WO-9404027 A1 * | 3/1994 | ............. | A01N 25/24 |
| WO | WO-2013095993 A2 * | 6/2013 | ............... | A61K 8/35 |

OTHER PUBLICATIONS https://www.dow.com/documents/en-us/productdatasheet/119/119-01882-01-triton-x100-surfactant-tds.pdf, Jan. 2023 (Year: 2023).*

Gower, M.D., The Effect of Varied Monomer Composition on Adhesive Performance and Peeling Master Curves for Acrylic Pressure-Sensitive Adhesives; published on-line Jul. 16, 2004 in Wiley Interscience (www.interscience.wiley.com); pp. 2909-2917.

Marcel Dekker Inc., Parouti, Sophia et al., A Comprehensive Experimental Investigation of the Methyl Methacrylatel Butyl Acrylate Acrylic Acid Emulsion Terpolymerization; Polymer Reaction Engineering, vol. 11, No. 4, pp. 829-853, 2003.

Kashmira Kathe; Harsha Kathpalia; Film forming systems for topical and transdermal drug delivery; Asian Journal of Pharmaceutical Sciences 12 (2017); pp. 487-497, (avbailable for download at https://www.sciencedirect.com/science/article/pii/S1818087617301538).

* cited by examiner

IN SITU PEELABLE PROTECTIVE BARRIER FILMS

I. BACKGROUND OF THE INVENTION

A. Field of Invention

The invention relates to the field of polymer films formed on the epidermis serving as protective barriers.

B. Description of the Related Art

There is a long-standing need for products that protect individuals' skin from contact with dirt and grease as well as illness-causing bacteria and viruses. Protection is especially important with respect to the hands, as the hands are naturally the body's most frequent contact surface. For example, a mechanic is more likely to soil his hands with grease than other parts of the body. Similarly, a food service worker must keep his hands in a sanitary condition while handling food. One very well-known solution to skin contaminants is to simply wash with soap and water. However, soap and water are not always readily available, especially when one is on public transportation, for instance. Moreover, soap tends to dry the skin, so repeated use can be damaging.

Hand sanitizing lotions are known which contain antiseptic ingredients such as ethanol, isopropanol, benzalkonium chloride and/or triclosan to kill bacteria and viruses. However, hand sanitizers have certain drawbacks. For example, the antiseptic ingredient wears off quickly and must be reapplied. Hand sanitizers also do nothing to remove soiling materials from the skin such as dirt and grease.

Certain barrier lotion products are known, a sampling of which includes Gloves in a Bottle®, Ghost Gloves®, and Invisible Glove®. Each product forms a protective barrier using ingredients such as dimethicone, glycerin, and paraffin wax. A clear drawback to such products is that they form a grease barrier rather than a peelable cohesive film. Such products either wear off or are washed off with soap and water. Further, none of these products form an effective barrier against chemical contaminants, heavy metals like lead, or against bacteria and viruses.

In situ film-forming compositions are known for skin applications, especially in wound care. However, all known compositions have significant problems. For example, Nexcare® forms a barrier film from siloxanes and acrylate terpolymer that is difficult to peel off. The Nexcare® packaging indicates that the "[p]roduct naturally wears off as skin heals." New Skin® and Skin Shield® both form fragile nitrocellulose films deposited from organic solvent systems including amyl acetate, ethyl acetate, ethyl alcohol, n-butyl acetate, acetone, and SD alcohol 40-B. Nitrocellulose films are intended to either wear off or be dissolved. The packaging for New Skin® states, "No remove, apply more New-Skin® Liquid Spray Bandage and quickly wipe off". None of the foregoing wound care products form peelable films.

It is also known to use cyanoacrylates as wound closures. For example, Vetbond™ is n-butyl cyanoacrylate. Cyanoacrylate films are brittle and not peelable without damaging the skin. Further, cyanoacrylates are known to have high vapor pressures and produce strong unpleasant chemical odors.

Natural and synthetic latexes are known for skin applications, such as in the field of costume makeup and special effects. While latexes are capable of forming peelable barriers, they have relatively long dry times on the order of minutes rather than seconds and form conspicuous opaque films. Furthermore, natural latexes are known to cause allergic reactions in some people.

Of course, examination gloves are also a well-known means for protecting the hands against soiling as well as bacterial and viral contaminants. However, gloves have numerous drawbacks as well. Like latex films, gloves are conspicuous and gloves made from natural latex rubber can cause allergic reactions. Although it is becoming more common to see individuals wearing examination gloves e.g., while grocery shopping or riding the subway, it is still uncommon and not generally perceived as aesthetically pleasing. From an alternative perspective, the fact that individuals are still willing to wear examination gloves in such contexts suggests a strong motivation to avoid illness-causing contaminants. As a practical matter, examination gloves must be changed frequently to maintain their sanitary effect. Therefore, one must carry extra gloves, which tends be bulky. A box of 100 gloves is generally the size of a facial tissue box.

What is needed is a composition that can be applied to the skin like a lotion, but quickly forms a peelable barrier film like a glove. Such a composition may advantageously be flexible, clear, discreet, and amenable to compact packaging.

II. SUMMARY OF THE INVENTION

Some embodiments may relate to an acrylic random copolymer consisting essentially of between 1 to 3 wt %+/−0.5 wt % acrylic acid, between 21 to 41 wt %+/−0.1 wt % n-butyl acrylic acid, 25 to 59 wt %+/−0.1 wt % methyl methacrylic acid, and between 19 to 34 wt %+/−0.1 wt % 2-ethylhexyl acrylic acid.

Other embodiments relate to an acrylic random copolymer consisting essentially of between 4 to 5 wt %+/−0.5 wt % acrylic acid, between 26 to 37 wt %+/−0.1 wt % n-butyl acrylic acid, 21 to 47 wt %+/−0.1 wt % methyl methacrylic acid, and between 26 to 33 wt %+/−0.1 wt % 2-ethylhexyl acrylic acid.

Still other embodiments relate to an emulsion of 40 to 55 wt % bimodal acrylic random copolymer consisting essentially of between 1 to 3 wt %+/−0.5 wt % acrylic acid, between 21 to 41 wt %+/−0.1 wt % n-butyl acrylic acid, 25 to 59 wt %+/−0.1 wt % methyl methacrylic acid, and between 19 to 34 wt %+/−0.1 wt % 2-ethylhexyl acrylic acid; 44 to 59 wt % water; buffer present in an amount effective to maintain a pH between 4 and 10; and a non-ionic surfactant present between 0.1 and 1.0 wt %.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein.

IV. DETAILED DESCRIPTION OF THE INVENTION

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

Headings are used herein for the sake of convenience and are not intended to affect the meaning or scope of the specification and/or claims, but rather to make the specification more readily understandable. Headings should not be used to construe the meaning of any of the teachings set forth herein, or to limit the scope of the claims.

Terms of degree, terms of approximation, and/or subjective terms may be used herein to describe certain features or elements of the invention. In each case sufficient disclosure is provided to inform the person having ordinary skill in the art in accordance with the written description requirement and the definiteness requirement of 35 U.S.C. 112.

Embodiments may comprise a polymeric protective barrier for the hands or other areas of the body. The barrier may be specially adapted to short duration use after which it may be conveniently peeled off in more or less one piece and discarded. It may be particularly advantageous for embodiments to be discreet, fast-hardening, crack resistant, peelable, and non-irritating to the skin. Embodiments may be applied in the manner of a lotion, and may harden to a mechanically stable and pliable film on a timescale of seconds to minutes.

Film Thickness

The thickness of some embodiments in a dried film form may be on the order of the thickness of a typical examination glove having a few mils thickness. For illustration, and without limitation, an embodiments' thickness may be 2-8 mils. It is contemplated that greater thicknesses such as 9-25 mils or greater may be advantageous for certain embodiments and applications. Film thickness and discreetness are inversely related. Therefore, it is desirable to minimize thickness to maximize discreetness. However, the strength of a film formulation factors into the lower limit of thickness because suitable films advantageously are sufficiently strong to withstand the forces applied by a wearer to peel the film from the skin. Accordingly, lower Young's-modulus film embodiments will tend to be thicker than higher Young's-modulus film embodiments. Additionally, films providing protection from viral contaminants must be sufficiently thick to account for the rate of viral filtration through the film. Thus, viral filtration rate also factors into the minimum thickness of a dried film embodiment, as embodiment films are contemplated to confer protection from virus particles for an amount of time. A suitable film thickness, according to embodiments of the invention, is determined by a plurality of interrelated factors including, without limitation, tensile strength, peel strength, film uniformity, viral filtration rate, and desired barrier properties.

Film Uniformity

Another desirable and advantageous property of some embodiments is a self-leveling property. Since embodiment films are applied similar to a lotion e.g., by rubbing the composition between one's hands, it is not feasible to expect the user to carefully apply the composition so that it forms a uniform film. Rather, the embodiment may form a uniform film spontaneously in response rubbing a film precursor emulsion on the skin in the manner of a lotion. The ordinarily skilled artisan will appreciate that suitable films of the invention need not be perfectly uniform in thickness. Rather, uniformity is acceptable when the thinnest part of the film is sufficiently strong to resist tearing during peel-off, while the thickest part of the film remains suitably discreet.

The degree of uniformity may be expressed as a standard deviation ($\sigma$) in film thickness. Standard deviations within the scope of the invention may vary and may depend in part on certain mechanical properties of a particular embodiment. For instance, a tougher or more cohesive film embodiment may tolerate a less uniform film thickness without failing and/or without fragmenting during peel-off. Conversely, a less-tough or less-cohesive film embodiment may tend to develop excessively weak regions that cannot tolerate forces applied during peel-off and/or within a predetermined range defined as normal wear.

Drying or Hardening Time

As used herein, the term hardening or hardened, as it relates to embodiments in film form or coating form, as in fast-hardening, means to solidify or gel from a liquid state or emulsion. The word "harden" is only intended to indicate the transition from liquid to solid. Hardening in this context does not mean that the solidified product is inflexible or stiff, nor is it intended to restrict embodiments to crosslinked polymers, or to restrict embodiments to a chemical process such as curing, or to a physical process such water or solvent evaporation.

The term dry time is used herein to indicate a result of a test for determining a time interval for a film to sufficiently harden so that it maintains its integrity while being subjected to certain physical conditions. The dry time determined according to these measurements is not intended to necessarily be equal to the time between the initial application of a precursor liquid e.g., an emulsion, and the time when a user would perceive the film to be ready for use. In fact, it is contemplated that drying may continue for a significant period after the user perceives the film as being ready to use. It is further contemplated that the user's perception would depend on factors such as whether the film feels tacky or wet to the extent of being uncomfortable. Since such perceptions are inherently subjective, and thus may vary substantially from one person to another, embodiment films of the invention are characterized instead by dry times as defined above and discussed in more detail herein.

The terms drying time and hardening time are used interchangeably herein. Suitable drying times of embodiments are on the order of seconds. Drying is sufficiently slow to provide enough working time for a user to apply the embodiment, but sufficiently fast to avoid requiring the user to wait idly for long periods of time, waiting for the embodiment to be perceived as ready for use. Some embodiments may be applied and function as a protective barrier almost immediately, even while the film is still hardening. Time ranges within the scope of the invention include without limitation between 1 and 10 seconds±0.5 seconds, 10 and 20 seconds±0.5 seconds, 20 and 30 seconds±0.5 seconds, 30 and 40 seconds±0.5 seconds, 40 and 50 seconds±0.5 seconds, and/or 50 and 60 seconds±0.5 seconds, or any combination thereof.

Some embodiments may be applied under conditions that permit longer hardening times without seeming objectionable to the user. For instance, a hardening time on the order of minutes to as much as 15 minutes±3 minutes may be suitable for certain applications on surfaces other than that of the palms of the hands. In general, longer hardening times become more tolerable to a user the less it interferes with the user's activities. Accordingly, an embodiment film deposited on the skin of a user's palms may require a faster hardening time than an embodiment applied elsewhere.

Crack Resistance

Suitable films within the scope of the present invention also resist cracking during the drying process. Crack resistance according to some embodiments of the invention may include resistance to capillary forces that result from evaporation of a liquid phase from a drying latex emulsion or from a gel such as a hydrogel or alcogel. Crack resistance according to embodiments of the invention may also include resistance to applied forces such as shear forces and compressive forces. For example, embodiment films applied to the hands are at least capable of resisting fracture and cracking when the user engages in most ordinary activities such as gripping a railing, turning a doorknob, opening a car door, or buttoning and unbuttoning clothes. Embodiments may also be sufficiently cohesive and tough to be peeled off the skin in more or less one piece. Suitable materials need not be peelable in exactly one piece, or without tearing, cracking, or fracture to any degree. Rather embodiments may be conveniently removed from the skin without expending undue time and effort.

Compositions and Formulations

Waterborne latexes provide certain advantages, one of which is in the number of different monomers that can be used to make a synthetic latex polymer. This allows the ordinarily skilled artisan to choose from a wide variety of commercially available inexpensive feedstocks to synthesize compounds for forming sanitary barrier films. Accordingly, mechanical and thermal properties of the film can be adjusted or tuned by varying the monomers used and their proportions relative to each other. For example, properties such as glass transition temperature, elasticity, peel strength, minimum film formation temperature (MFFT), and to a limited extent even dry time can be tuned in this way.

Embodiments of the invention may include synthetic waterborne latex-forming compounds. Specifically, embodiments include copolymer latex formulations of 2-ethylhexyl acrylate (EHA), butyl acrylate (BA), methyl methacrylate (MMA), and acrylic acid (AA). Embodiments incorporate the foregoing monomers in a range of relative percentages. In the broadest view, embodiments consist essentially of copolymers of the foregoing monomers where AA is present between 1-2 wt %, and EHA, BA and MMA each independently vary between 1-97 wt %. However, embodiments may include AA between 1-5 wt % provided the foregoing ranges are constrained so that BA is between 21-41 wt %, MMA is between 25-97 wt %, and EHA is between 19-34 wt %. The monomers are represented herein according to the following structural formulae indicating the molecular species and the polymeric subunit.

Example I: Two-Stage Process with Vinyl Acetate

Stage I: Seed Synthesis

A seed synthesis may be performed in an Optimax reactor, available from Mettler Toledo, equipped with a heating jacket, a mechanical stirrer, nitrogen inlet/outlet ports, and a reflux condenser. The initial charge to the reactor contains buffer, sodium bicarbonate (0.50 g), initiator, sodium dodecyl sulfate (0.33 g) and deionized water (50 g). The initial charge is stirred at 400 rpm and heated to 75° C. A monomer solution is then made by first adding sodium bicarbonate (0.03 g) and sodium dodecyl sulfate (1.0 g) to deionized water (26.67 g). This is stirred until a clear solution is formed, and then monomer (26.67 g) is added. An initiator solution is also made by dissolving ammonium persulfate (0.80 g) in deionized water (33.33 g). The initiator and monomer solutions are added dropwise over 2 h. The reaction is then stirred at 400 rpm and 75° C. for 2 h.

Stage II: Synthesis of poly(2-ethylhexyl acrylate)-co-(butyl acrylate)-co-(vinyl acetate)-co-(methylmethacrylate)

A latex copolymer containing 18 wt % EHA, 18 wt % BA, 36 wt % VAc, and 29 wt % MMA is made. These percentages are calculated based upon the mass of each monomer added substantially all of the monomers are incorporated into the resulting polymer. Some residual monomer is expected. Thus, the wt % of each monomer incorporated into the polymer may vary by +/−0.5%. The latexes may be made in an Optimax reactor, equipped with a heating jacket, a mechanical stirrer, nitrogen inlet/outlet, and a reflux condenser. The seed solution (5.33 g) is charged to the reactor. The reactor is set to 55° C. with stirring at 300 rpm under a $N_2$ atmosphere. A monomer solution is made by adding surfactants, Triton X-100 (0.64 g) and sodium dodecyl sulfate (0.16 g), and sodium bicarbonate buffer (0.03 g) to deionized water (26.67 g). This solution is stirred until all solids are dissolved, and then the monomers (26.67 g) are added. An initiator solution is also made by adding ammonium persulfate (0.80 g) to deionized water (33.33 g). The initiator and monomer solutions are added to the reactor dropwise over 2 h. The reaction is stirred at 300 rpm and 55° C. for 4 h.

This formulation has very significant drawbacks. First the inclusion of vinyl acetate tends to produce slightly opaque films, which runs counter to the goal of a discreet film. Vinyl acetate also tends to destabilize the emulsion resulting in emulsions with relatively low percent solids and therefore higher water content. This runs counter to the goal of a fast-dying formulation. Vinyl acetate is also known to increase film porosity. This tends to diminish effectiveness of the film in providing a sanitary barrier against viral and bacterial contaminants. More porous films are expected to permit particles to defuse more rapidly through the film and contaminate underlying skin. Finally, the inclusion of a seed particle synthesis in this example is effective in controlling particle size, producing a comparatively monodisperse emulsion. However, such control not only adds steps to the production process, it extends dry time. Bimodal or polydisperse latex particles tend to pack more efficiently during film formation thereby better excluding water from the film and decreasing dry time.

Example II. Single-Pot Synthesis without Vinyl Acetate (JH3-48-1)

A latex copolymer containing 2.88 wt % AA, 30.91 wt % BA, 37.01 wt % MMA, and 29.20 wt % EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. The reaction described in this example goes substantially to completion. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.208 g, 2.89 mmol), 2-ethylhexyl acrylate (2.109 g, 11.44 mmol), methyl methacrylate (2.673 g, 26.7 mmol), butyl acrylate (2.232 g, 17.4 mmol), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for two hours. Reflux within the vial is achieved by passing nitrogen over the portion of the vial that is not submerged in oil.

Example III. Single-Pot Synthesis without Vinyl Acetate (JH3-53-1)

A latex copolymer containing 2.88 wt % AA, 30.91 wt % BA, 37.01 wt % MMA, and 29.20 wt % EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.208 g, 2.89 mmol), 2-ethylhexyl acrylate (2.109 g, 11.44 mmol), methyl methacrylate (2.673 g, 26.7 mmol), butyl acrylate (2.232 g, 17.4 mmol), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

A similar preparation denoted herein as JH3-96-1 is identical to JH3-53-1 described above except that the preparation of the former is at a roughly 10× scale compared to the latter.

Example IV. Single-Pot Synthesis without Vinyl Acetate (JH3-53-2)

A latex copolymer containing 2.88 wt % AA, 30.91 wt % BA, 37.01 wt % MMA, and 29.20 wt % EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g), and sodium bicarbonate (0.068 g). The mixture is heated to 75° C. and stirred at 300 rpm until a clear solution is obtained. Separately, a monomer solution is prepared by combining acrylic acid (0.208 g, 2.89 mmol), 2-ethylhexyl acrylate (2.109 g, 11.44 mmol), methyl methacrylate (2.673 g, 26.7 mmol), butyl acrylate (2.232 g, 17.4 mmol), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for two hours. Reflux within the vial is achieved by passing nitrogen over the portion of the vial that is not submerged in oil. At the end of two hours, additional initiator is added, specifically, 0.091 g ammonium persulfate in 1.137 g of water, and the reaction continued under reflux for an additional two hours.

Example V. Single-Pot Synthesis without Vinyl Acetate

A latex copolymer containing 2.88 wt % (19.3 mmol) AA, 30.90 wt % (116.3 mmol) BA, 37.02 wt % (178.3 mmol) MMA, and 29.20 wt % (76.41 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remained stable with time, and yields a clear, flexible, peelable film when applied to a surface around 25° C. to 37° C. Prior to synthesis, inhibitors are removed from butyl acrylate, methyl methacrylate, and 2-ethylhexyl acrylate by passing the liquid monomers through a short column of basic aluminum oxide. The monomers can be subsequently stored in a refrigerator until use.

The chemical reagents used synthesis of this embodiment emulsion are summarized in Table with example masses yielding 100 g of latex solution. The Final Mixture noted in Table I is the theoretical combination of Solutions 1, 2, and 3 prior to accounting for chemical reactions.

TABLE I

Reagents for latex synthesis.

| | Chemical | Mass [g] | Mass fraction [%] |
|---|---|---|---|
| Solution 1 | 0.1% Aqueous PVA | 22.76 | 98% |
| | Triton X-100 | 0.06 | 0.26% |
| | Sodium Dodecyl Sulfate | 0.06 | 0.26% |
| | Sodium Bicarbonate | 0.46 | 2% |
| | Total | 23.34 | 100% |
| Solution 2 | 0.1% Aqueous PVA | 12.14 | 20% |
| | Triton X-100 | 0.24 | 0% |
| | Sodium Dodecyl Sulfate | 0.24 | 0% |
| | Sodium Bicarbonate | 0.03 | 0.0% |
| | Butyl Acrylate | 14.90 | 24% |
| | Methyl Methacrylate | 17.85 | 29% |
| | 2-Ethylhexyl Acrylate | 14.08 | 23% |
| | Acrylic Acid | 1.39 | 2% |
| | Total | 60.88 | 100% |
| Solution 3 | 0.1% Aqueous PVA | 15.18 | 96% |
| | Ammonium Persulfate | 0.61 | 4% |
| | Total | 15.78 | 100% |
| Final Mixture | 0.1% Aqueous PVA | 50.08 | 50% |
| | Triton x-100 | 0.30 | 0.3% |
| | Sodium Dodecyl Sulfate | 0.30 | 0.3% |
| | Sodium Bicarbonate | 0.49 | 0.5% |
| | Ammonium Persulfate | 0.61 | 0.6% |
| | Butyl Acrylate | 14.90 | 15% |
| | Methyl Methacrylate | 17.85 | 18% |
| | 2-Ethylhexyl Acrylate | 14.08 | 14% |
| | Acrylic Acid | 1.39 | 1% |
| | Total | 100.00 | 100% |

Reagents are used as received from the vendor unless otherwise noted. Prior to synthesis, the liquid monomers are passed through a short column of basic aluminum oxide to remove inhibitors. A stock solution of 0.1% aqueous polyvinyl alcohol (PVA) is prepared via dissolution of 0.5 g of PVA ($M_w$ 13,000-23,000 g/mol) in 500 mL of deionized (DI) water. Solution 1 (suspension solution) is prepared by combining Triton X-100, sodium dodecyl sulfate (SDS), sodium bicarbonate, and 0.1% aqueous PVA in a 250 mL, three-neck round bottom flask equipped with two addition funnels, a reflux condenser, and a magnetic stir bar. The flask is submerged in a hot oil bath, and the mixture is heated at 75° C., with stirring at 300 rpm, until a clear solution is achieved.

Separately, a monomer solution (Solution 2) and an initiator solution (Solution 3) are prepared. For Solution 2, butyl acrylate, methyl methacrylate, 2-ethylhexyl acrylate, and acrylic acid are added to a solution of Triton X-100, SDS, and sodium bicarbonate in 0.1% aqueous PVA. For Solution 3, ammonium persulfate is dissolved in 0.1% aqueous PVA. After transfer to the two addition funnels, Solution 1 is continuously stirred at 300 rpm and 75° C. Solution 2 and Solution 3 are then added dropwise, in parallel, to the round bottom flask at rates of approximately 0.90 mL/min and 0.24 mL/min, respectively. Once all three solutions are combined, the reaction mixture is heated under a reflux condenser at 75° C. with stirring at 300 rpm for 4 hours. The resultant opaque white liquid latex is removed from heat and stored at room temperature. Coating the opaque latex solution onto a surface yields a clear, flexible film upon drying. Drying times are under 60 seconds for a nominal film thickness of 70 μm and approximately 50 wt % solids. The latex of this Example II is shown via thermogravimetric analysis (TGA) to contain approximately 51 wt % solids. Dynamic light scattering yields a bimodal distribution of number-average particle diameters with peaks at 160 nm and 390 nm.

Example VI. Single-Pot Synthesis without Vinyl Acetate

A latex copolymer containing 2.88 wt % (779 mmol) AA, 30.90 wt % (4690 mmol) BA, 37.02 wt % (7193 mmol) MMA, and 29.20 wt % (3083 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. A 4000 g batch of an embodiment emulsion is made according to the following procedure. A reaction vessel is charged with 968.3 g DI water, 188.0 g of 1% polyvinyl alcohol, 4.0 g sodium lauryl sulfate sold under the trademark Polystep® B-5, and 2.4 g sodium bicarbonate. The reactor is purged with nitrogen for 20 minutes and heated to 75° C.

In a second container, a pre-emulsion is prepared from 441.0 g DI water, 17.3 g Triton X-405, 80.7 g sodium lauryl sulfate sold under the trademark Polystep® B-5, 720.2 g methyl methacrylate, 568.1 g 2-ethylhexyl acrylate, 601.2 g butyl acrylate, and 56.1 g acrylic acid. In a third container a first initiator charge is prepared from 47.2 g sodium persulfate and 1.2 g DI water. In a fourth container a second initiator charge is prepared from 161.4 g sodium persulfate and 6.1 g of DI water.

At about 70° C. 124 g (5%) of pre-emulsion is added to the reactor followed by the first initiator charge. At about 80° C. the remaining pre-emulsion is added slowly over the course of four hours at a rate of 10 g/s. Simultaneously, the second initiator charge is added of the same period at a rate of 0.084 g/s. When feeds are complete, the temperature is maintained between 80° C. and 83° C. for thirty minutes and then cooled to 65° C. At 65° C. the cleanup reagent is then added slowly over the course of thirty minutes. The reactor is cooled to 40° C. and the emulsion is tested for percent solids. DI water is added as needed to adjust solids content. The pH of the emulsion is adjusted with ammonium hydroxide. The resulting emulsion has a viscosity of about 1700 cps, pH of 5.44, and a solids content of 50.65%.

Example VII. Single-Pot Synthesis without Vinyl Acetate

A latex copolymer containing 2.32 wt % (2.34 mmol) AA, 30.95 wt % (17.53 mmol) BA, 37.07 wt % (26.88 mmol) MMA, and 29.66 wt % (11.69 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.168 g, 2.34 mmol), 2-ethylhexyl acrylate (2.153 g, 11.69 mmol), methyl methacrylate (2.691 g, 26.88 mmol), butyl acrylate (2.247 g, 17.53 mmol), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example VIII. Single-Pot Synthesis without Vinyl Acetate

A latex copolymer containing 3.48 wt % (3.51 mmol) AA, 29.92 wt % (16.94 mmol) BA, 35.46 wt % (25.71 mmol) MMA, and 31.15 wt % (12.27 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.253), 2-ethylhexyl acrylate (2.261 g), methyl methacrylate (2.574 g), butyl acrylate (2.172 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example IX. Single-Pot Synthesis without Vinyl Acetate

A latex copolymer containing 2.33 wt % (2.34 mmol) AA, 29.02 wt % (16.36 mmol) BA, 38.86 wt % (28.05 mmol) MMA, and 29.80 wt % (11.69 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.1684), 2-ethylhexyl acrylate (2.153 g), methyl methacrylate (2.808 g), butyl acrylate (2.097 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example X. Single-Pot Synthesis without Vinyl Acetate

A latex copolymer containing 1.13 wt % (1.17 mmol) AA, 29.26 wt % (16.95 mmol) BA, 36.25 wt % (26.88 mmol) MMA, and 33.36 wt % (13.44 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.0842), 2-ethylhexyl acrylate (2.477 g), methyl methacrylate (2.691 g), butyl acrylate (2.172 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XI. Single-Pot Synthesis without Vinyl Acetate

A latex copolymer containing 4.74 wt % (4.67 mmol) AA, 29.48 wt % (16.36 mmol) BA, 37.01 wt % (26.29 mmol) MMA, and 29.77 wt % (11.10 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.337 g), 2-ethylhexyl acrylate (2.046 g), methyl methacrylate (2.633 g), butyl acrylate (2.097 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XII. Single-Pot Synthesis without Vinyl Acetate

A latex copolymer containing 2.39 wt % (2.34 mmol) AA, 21.26 wt % (11.69 mmol) BA, 47.32 wt % (33.31 mmol) MMA, and 29.03 wt % (11.10 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.168 g), 2-ethylhexyl acrylate (2.046 g), methyl methacrylate (3.335 g), butyl acrylate (1.498 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XIII. Single-Pot Synthesis without Vinyl Acetate

A latex copolymer containing 1.73 wt % (1.75 mmol) AA, 41.08 wt % (23.37 mmol) BA, 32.09 wt % (23.37 mmol) MMA, and 25.10 wt % (9.933 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.126 g), 2-ethylhexyl acrylate (1.830 g), methyl methacrylate (2.340 g), butyl acrylate (2.996 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XIV. Single-Pot Synthesis without Vinyl Acetate

A latex copolymer containing 1.66 wt % (1.75 mmol) AA, 37.43 wt % (22.20 mmol) BA, 26.93 wt % (20.45 mmol) MMA, and 33.99 wt % (14.02 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.126 g), 2-ethylhexyl acrylate (2.584 g), methyl methacrylate (2.048 g), butyl acrylate (2.846 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XV. Single-Pot Synthesis without Vinyl Acetate

A latex copolymer containing 3.01 wt % (2.922 mmol) AA, 40.13 wt % (21.91 mmol) BA, 37.62 wt % (26.29 mmol) MMA, and 19.23 wt % (7.304 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.211 g), 2-ethylhexyl acrylate (1.346 g), methyl methacrylate (2.633 g), butyl acrylate (2.808 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Example XVI. Single-Pot Synthesis without Vinyl Acetate

A latex copolymer containing 1.88 wt % (1.75 mmol) AA, 21.23 wt % (11.10 mmol) BA, 57.61 wt % (38.56 mmol) MMA, and 19.28 wt % (7.012 mmol) EHA. These percentages are calculated based upon the mass of each monomer added and assumes that substantially all of the monomers are incorporated into the resulting polymer. Some residual monomer is expected. Thus, the wt % of each monomer incorporated into the polymer may vary by +/−0.5%. Furthermore, the weight percentages given pertain only to the composition of the copolymer molecule without regard to other materials that may be dissolved in the copolymer. This example synthesis of an embodiment emulsion yields a latex formulation that dries rapidly, remains stable with time, and yields a clear, flexible, peelable film when applied to a surface at 37° C. Prior to synthesis, inhibitors are removed by passing the liquid monomers through a short column of basic aluminum oxide. The monomers can be subsequently stored in a refrigerator until use.

The following reagents are combined in a 20 mL glass vial equipped with a stir bar and submerged in a hot oil bath: 0.1% aqueous polyvinyl alcohol (3.409 g) having a molecular weight ($M_w$) between 13,000-23,000 g/mol, sodium dodecyl sulfate (0.009 g), Triton X-100 (0.009 g) and sodium bicarbonate (0.068 g). The mixture is heated to 75° C. and stirred at 300 rpm until a clear solution is obtained. Separately, a monomer solution is prepared by combining acrylic acid (0.126 g), 2-ethylhexyl acrylate (1.292 g), methyl methacrylate (3.861 g), butyl acrylate (1.423 g), sodium bicarbonate (0.005 g), sodium dodecyl sulfate (0.036 g), Triton X-100 (0.036 g) and 0.1% aqueous PVA (1.818 g). An initiator solution is prepared by combining ammonium persulfate (0.091 g) and 0.1% aqueous PVA (2.273 g). The monomer and initiator solutions are loaded into separate 10 mL disposable syringes and are added dropwise to the solution within the 20 mL glass vial over a period of 10 minutes. Once both solutions are added, the reaction mixture is refluxed at 75° C. for four hours. Reflux within the vial is achieved by passing nitrogen over the portion of the vial that is not submerged in oil.

Emulsion Characterization

Particle Size

Particle size and distribution can be measured through known dynamic light scattering methods. Dynamic light scattering methods measure fluctuations in scattered light intensity of a polymer solution to calculate particle size and polydispersity. In general, a monochromatic source such as a laser is polarized and impinges the sample. Each particle diffracts light in all directions, and each diffracted photon wave interferes constructively or destructively with the scattered photons around it, thus producing an interference pattern which is projected through a second polarizer and a two-dimensional image is constructed showing a speckled two-dimensional interference pattern. Since the polymer particles are in motion the interference pattern changes as a function of time. Accordingly, the rate at which any given spot changes is related to the size of the particle, larger particles naturally moving more slowly than smaller particles. Spots that change at the same rate have the same autocorrelation function, $g^2$ (Eq. 1). One can conclude that spots with similar autocorrelation functions have similar masses. Accordingly, histograms of like $g^2$ values can be constructed and arranged from low to high, collectively tracing out a distribution of particle sizes. Typically, particle size is shown on the x-axis and relative amount is shown on the y-axis.

$$g^2(q,\tau) = \langle I(t)I(t+\tau)\rangle / \langle I(t)\rangle^2 \qquad \text{(Eq. 1)}$$

In Equation I (Eq. 1), q is the wave vector, τ is time delay and I is intensity.

A suitable experimental methodology for particle size distribution analysis involves dispensing sample solutions into disposable Sarstedt micro-cuvettes for measurement with a Zetasizer Nano ZS90 particle size analyzer. Measurements are performed with the following conditions:

Equilibration time: 30 seconds
Temperature: 25° C.
Measurement angle: 90°
Measurement duration: automatic
Dispersant: Water with a viscosity of 0.882 cP and a refractive index of 1.33
Number of measurements: 3

Both intensity and number-based particle size distributions (PSDs) are reported for the nanoparticles and are generated by combining the results of the three measurements. Although intensity is the basic distribution obtained directly from dynamic light scattering measurements, the number distribution provides a relative indication of the number of particles at a given size. Larger particles scatter more light than smaller particles, with scattering intensity proportional to the sixth power of particle diameter. The particle sizes and standard deviations for each peak within the intensity and number-based PSDs are determined. Standard deviation in this context is an indicator of peak width.

In addition to the PSDs, a cumulant size, referred to as the z-average size, and the polydispersity index (PDI) is reported for each sample. These values are calculated following ISO 13321 (Particle Size Analysis-Photon Correlation Spectroscopy) and assume that the particles in solution are monomodal and spherical in shape. If the underlying particle distribution is monodisperse, the z-average size will be the same as the mean of the peak in the distribution. However, if the underlying distribution is polydisperse, the z-average size will differ from the sizes of the two or more observed peaks. PDI can range from 0 to 1, with 1 indicating a highly polydisperse sample. The average and standard deviation of the z-average sizes and PDIs of the three measurements for each sample are calculated.

Figure 1:
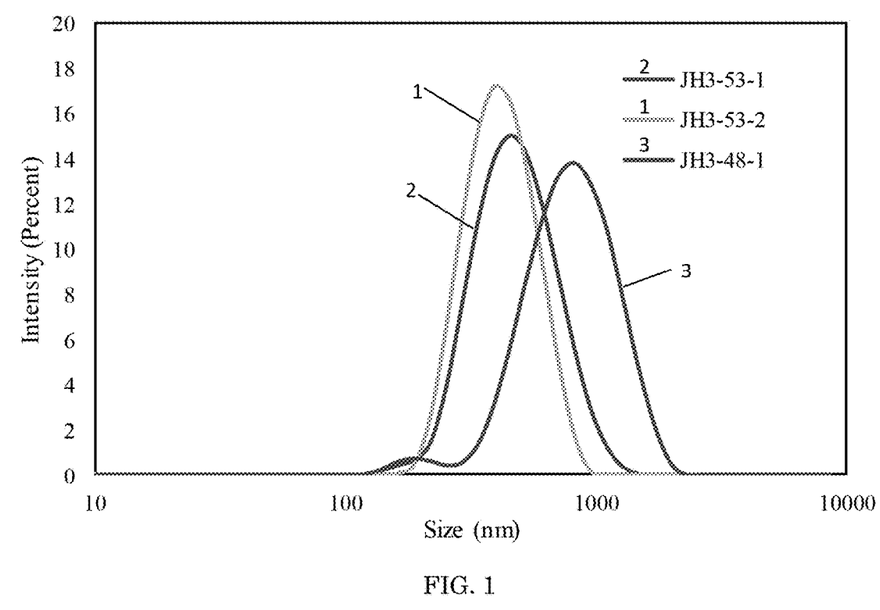
FIG. 1 is a dynamic light scattering plot of intensity versus particle size for three embodiment emulsions.
Figure 2:
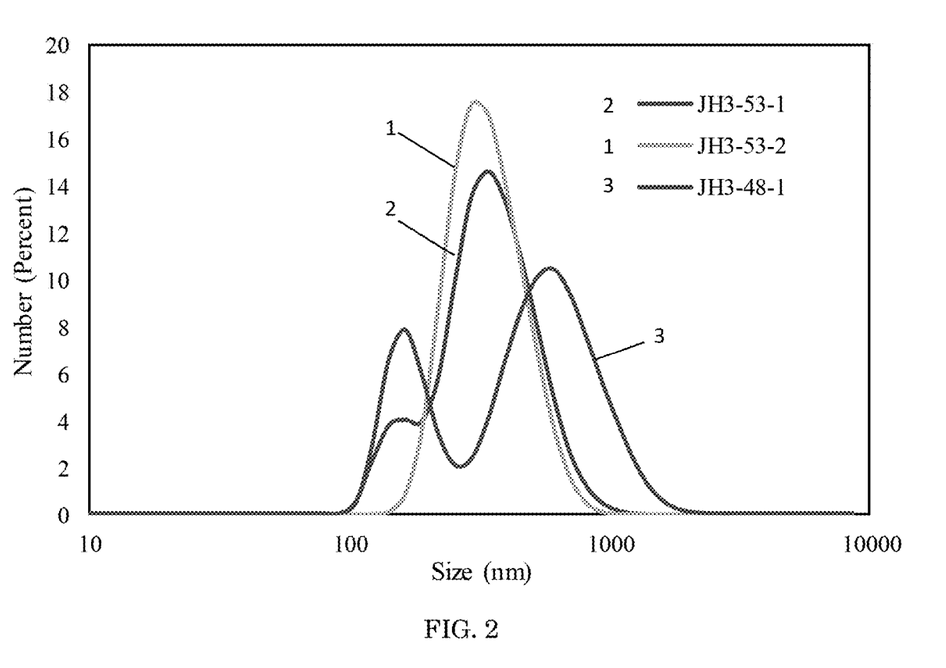
FIG. 2 is a dynamic light scattering plot of number versus particle size for three embodiment emulsions.

Particle size distributions (PSDs), z-average particle sizes, and polydispersity indices observed for three example embodiments JH3-48-1, JH3-53-1, and JH3-53-2 are summarized in Table II. Overlays of the intensity-based distributions and number-based distributions for the three example embodiments are provided in FIGS. 1 and 2, respectively. Embodiment JH3-53-2 is peak 1, embodiment JH3-53-1 is peak 2, and embodiment JH3-48-1 is peak 3. The particle size distributions for the three examples show a substantial amount of overlap; however, the z-average sizes for samples JH3-48-1 and JH3-53-1 indicates a bimodal particle size distribution in the intensity-based (FIG. 1) and/or number-based (FIG. 2) PSDs. In contrast, embodiment JH3-53-2 is substantially monodisperse, with only a single peak in the intensity and number-based PSDs.

TABLE II

|  |  | JH3-48-1 | JH3-53-1 | JH3-53-2 |
|---|---|---|---|---|
| Intensity PSD | Peak 1 | 857.5 ± 331.1 (97.3) | 507.8 ± 195.7 (100.0) | 435.2 ± 137.2 (100.0) |
|  | Peak 2 | 195.8 ± 2.7 (36.01) | n/a* | n/a* |
| Number PSD | Peak 1 | 649.2 ± 271.5 (71.5) | 156.7 ± 25.64 (14.0) | 354.7 ± 119.5 (100.0) |
|  | Peak 2 | 172.5 ± 36.79 (28.5) | 386.7 ± 144.6 (86.0) | n/a* |
|  | Z Avg Size | 699.37 ± 5.67 | 446.77 ± 3.89 | 403.33 ± 3.61 |
|  | PDI | 0.171 ± 0.037 | 0.153 ± 0.017 | 0.121 ± 0.040 |

*n/a indicates that this peak is not present within the distribution

Table II provides intensity and number particle size distributions (PSDs) for each of three polymer emulsion embodiments, including particle size and standard deviation for each peak within the distributions. The relative particle amount for each peak is given as a percentage of the total particle amount within the parentheses.

Thermogravimetric Analysis (TGA) of solids content

Thermogravimetric Analysis (TGA) is used to evaluate the solids content of embodiment emulsions. The methodology is carried out on a TA Instruments Q500 TGA. Sample droplets are placed in cleaned and tared platinum pans. The experimental conditions are as follows:

Sample Purge Flow: 90 mL/min
Balance Purge Flow: 10 mL/min
Purge Gas: Nitrogen

Temperature Program:
Ramp 10.00° C./min to 155.00° C.
Isothermal for 60.00 min at 155.00° C.

Figure 3:
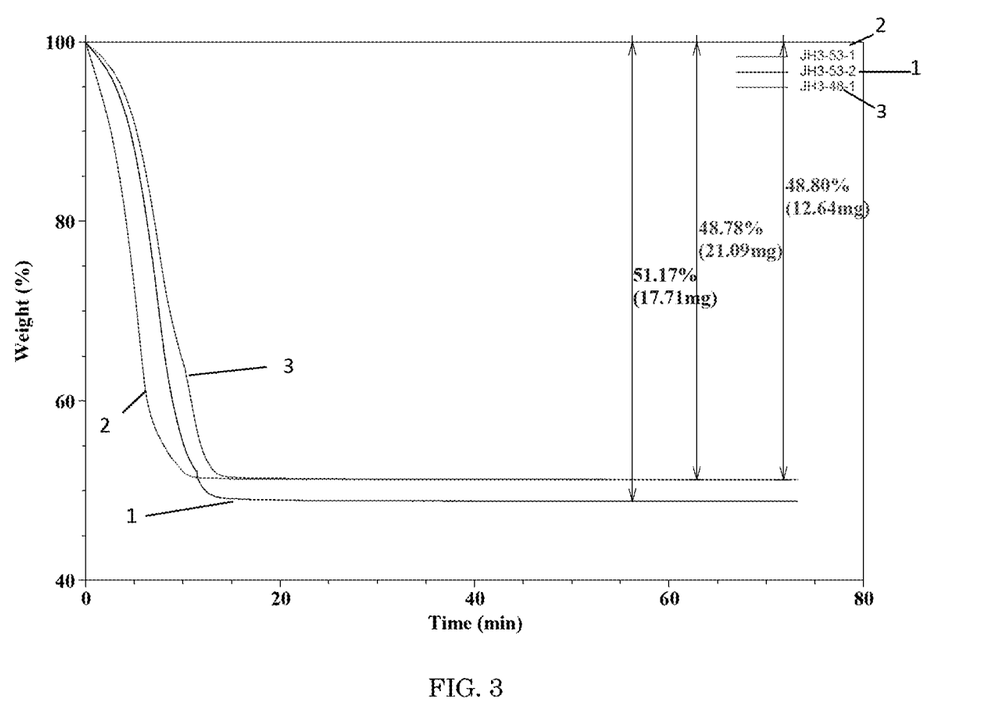
FIG. 3 is a thermogravimetric analysis plot for three embodiments.

An overlay of the TGA curves obtained for sample embodiments JH3-48-1 (line 3), JH3-53-1 (line 2), and JH3-53-2 (line 1) is shown in FIG. 3. In all three samples water has boiled off by about 15 minutes leaving dry polymer residue. Percent solids is calculated as the ratio of residual mass to the starting mass. All three samples have a solids content of approximately 50%. The solids content values of each of the three samples are summarized in Table III. Variations are due to slight differences in starting masses. Preparation of embodiment JH3-53-2 includes the addition of aqueous initiator, which results in a slight decrease in the solids content relative to JH3-48-1 and JH3-53-1.

TABLE III

Solids Content.

| Embodiment | Solids Content [%] |
|---|---|
| JH3-48-1 | 51.22 |
| JH3-53-1 | 51.20 |
| JH3-53-2 | 48.83 |

Dry Time

Films embodiments are made from each of the emulsion embodiments discussed above. The films are formed on xylene-cleaned glass microscope slides using a doctor's blade to control film thickness and uniformity. Films of 50, 70 and 100 microns are made accordingly.

The person having ordinary skill in the art will be aware of a number of methods and instruments are known for measuring drying times. Temperature may be controlled to reflect average core body temperature (~37° C.), or an estimated extremity body temperature (~30° C.). One such device is a ball and stylus instrument available from Gardco. This type of device includes a stylus comprising an arm and ball assembly mounted to a motor shaft. The stylus is thus driven in a circular arc at a constant speed over the surface of a drying sample. The sample is deemed dry when the stylus no longer marks the sample. Since this stylus moves at a constant speed for a known time across a known path length, the dry time can be accurately deduced from the point in the arc path where the marking ends. Dry time does not indicate the point after which a sample loses no further moisture, or does not continue to coalesce, beyond the dry time. Drying may continue past the point when it is deemed dry by this method. The dry point according to this methodology simply means that the sample has reached a sufficient degree of hardening that stylus no longer marks the sample.

Another method for determining dry time is based on the subjective perception of an observer. For example, a sample may be applied to a test surface, such as a glass slide, at a known thickness using a doctor blade. Time zero is the time of application, and the dry time is the time at which the sample is visually observed to be solid in response to impingement by a probe. Temperature may be controlled to reflect average core body temperature (~37° C.), or an estimated extremity body temperature (~30° C.). For instance, if the sample is resilient under the probe then it is deemed dry. Samples that are not tacky when dry may also be probed for tackiness to determine dry time. A suitable probe may be a common glass stir rod or metal spatula, for example.

Figure 4:
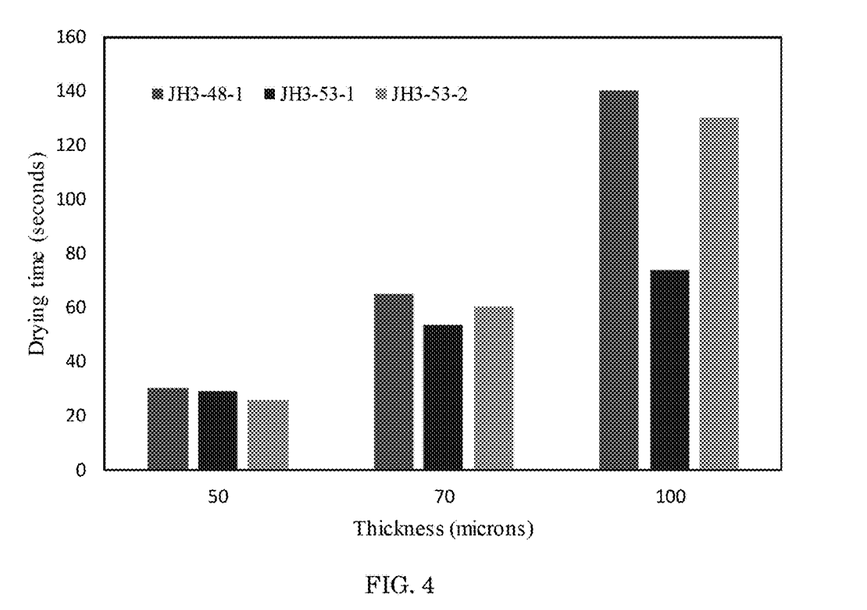
FIG. 4 is a plot of film thickness versus dry time for three embodiments.
Figure 5:
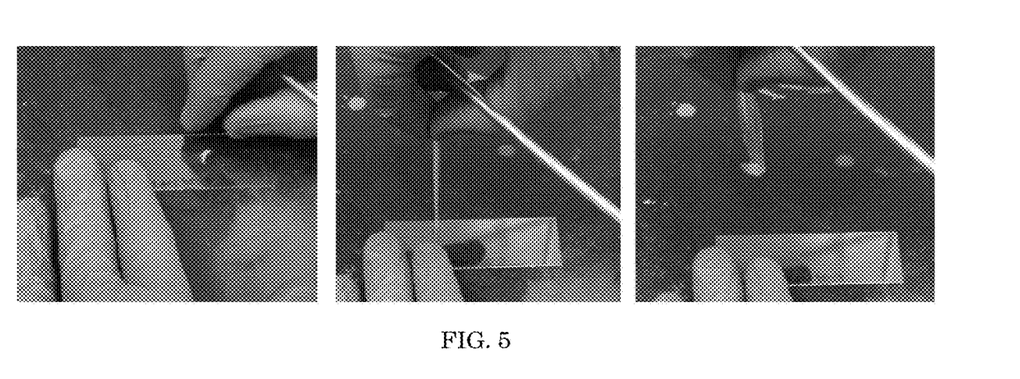
FIG. 5 is a series of three photographs showing an embodiment being peeled from a glass slide.

FIG. 4 shows the dry times of films of embodiments JH3-58-1, JH3-53-1, and JH3-53-2. Dry times of each sample are obtained for 50, 70, and 100 micron films. These data are also summarized in Tables VII and VII. FIG. 5 shows a film of embodiment JH3-48-1 being peeled from a glass slide. Table VIII summarizes dry time data for each of the three embodiments at 33° C. and a film thickness of 3.94 mils.

TABLE VII

Measured Dry Times on Glass at room temperature (~25° C.)

| Film Thickness | | Dry Time (s) | | | | | |
|---|---|---|---|---|---|---|---|
| (mils) | (μm) | JH3-48-1 | JH3-53-1 | JH3-53-2 | JH3-96-1 | JH3-153-1 | JH3-160-1 |
| 2.0 | 50 | 30 | 29 | 26 | | | |
| 2.8 | 70 | 65 | 53.5 | 60 | | | |
| 3.9 | 100 | 140 | 74 | 130 | | | |

TABLE VIII

Measured Dry Times on Glass at room temperature (~33° C.)

| Temperature (° C.) | Film Thickness (mils) | Film Thickness (μm) | Dry Time (s) JH3-96-1 | Dry Time (s) JH3-153-1 | Dry Time (s) JH3-160-1 |
|---|---|---|---|---|---|
| 33 | 3.94 | 100 | 78 | 113 | 97 |

Additives

Embodiments of the invention include water emulsions of the acrylate copolymer particles taught herein. Such emulsions may be stabilized through the addition of one or more buffers and/or one or more surfactants. The person having ordinary skill in the art will readily appreciate that a wide variety of combinations of buffers and surfactants can achieve the same stabilizing effect. It is contemplated that the skilled artisan will be readily capable of selecting appropriate combinations. However, several specific examples are provided as illustrations, and not as limitations to the invention.

The buffers and surfactants taught herein are not limited to ingredients Generally Recognized as Safe (GRAS), because the invention is not limited to films formed only on live skin and may include other surfaces as well. However, the person having ordinary skill in the art will readily appreciate and understand that embodiments formulated for skin application are preferably drawn from GRAS ingredients, and is capable of selecting ingredients accordingly.

Buffers according to embodiments of the invention preferably maintain the pH of the emulsion between about 7 and 10+/−10%, and more preferably between about 8 and 9+/−10%. Suitable buffers include, without limitation, bicarbonate; phosphate; citrate; glycine; borate; 2-Amino-2-methyl-1,3-propanediol; N,N-Bis(2-hydroxyethyl)taurine; 4-(2-hydroxyethyl)-1-piperazineethanesulfonic acid; imidazole; 3-Morpholinopropane-1-sulfonic acid; 3-{[1,3-dihydroxy-2-(hydroxymethyl)propan-2-yl]amino}propane-1-sulfonic acid; or 2-[[1,3-dihydroxy-2-(hydroxymethyl)propan-2-yl]amino]ethanesulfonic acid; N-(2-Hydroxy-1,1-bis(hydroxymethyl)ethyl)glycine.

Surfactants according to embodiments of the invention are non-ionogenic, thus not interfering with the buffer or buffer system of the emulsion. In one nonlimiting example, the surfactant is an aryl having an aliphatic substituent of C5-C16 and a polyethylene oxide substituent chain between 4 and 20 polyethylene oxide units long. In another nonlimiting example, the surfactant is a 1,4-aryl having an aliphatic substituent of C5-C16 and a polyethylene oxide substituent chain between 4 and 20 polyethylene oxide units long. One specific example of a surfactant within the scope of the invention is 2-[4-(2,4,4-trimethylpentan-2-yl)phenoxy]ethanol, sold under the trademark Triton-X 100®.

Emulsion embodiments may optionally include compounds for soothing, moisturizing, or healing the skin such as, without limitation, aloe, essential oils, mineral oil, petrolatum, lanolin, dimethicone, hyaluronic acid, glycerin, and any of a wide variety of compounds known to have emollient or humectant properties. The term essential oil is used herein according to its ordinary meaning, and is meant to include any plant-derived oil with a moisturizing property and/or with an appealing fragrance. For example, and without limitation, essential oils include oils known in the field of aroma therapy and/or oils extracted from herbs such as basil, oregano, cinnamon, peppermint, green tea, eucalyptus, lemongrass, orange, lavender, frankincense, rosemary, lemon, bergamot, cedarwood, patchouli, geranium, pink grapefruit, clove, and sage.

The person having ordinary skill in the art will understand that soothing or moisturizing components must be high enough in concentration to be effective, but low enough in concentration to avoid degrading emulsion stability or film performance. More specifically, the skilled artisan will understand that an effective amount of a moisturizer is that which has a moisturizing effect on the underlying skin sufficient to mitigate or counterbalance moisture losses due to use of the product. Similarly, an effective amount of a soothing additive is one that imparts a soothing effect to the underlying skin sufficient to mitigate or counterbalance any irritation due to use of the product, such as through repeated peel-off.

With respect to emulsion stability and film performance, moisturizing and soothing additives must be low enough in concentration so that they allow for a desirable degree of emulsion stability. A desirable degree of emulsion stability is readily ascertainable by the skilled artisan according to the subjectively desired shelf life of the emulsion. For instance, in some embodiments a shelf life of one to two years is desirable. It is well within the ordinary skill in the art to determine, without undue experimentation, an effective amount of an additive that also allows for a desirable degree of emulsion stability. Similarly, it is well within the skill in the art to determine, without undue experimentation, an effective amount of an additive that also allows for acceptable film performance properties, such as peel strength, cohesion during peel-off, and viral filtration rate.

Emulsion embodiments of the invention may optionally include one or more antiseptic ingredients as are known in the art to the person having ordinary skill. It is well within the ordinary skill of the art select an appropriate antiseptic in an amount effective to function as a preservative. Specifically, to prevent microbial growth during storage. Preservative additives will have comparatively little skin contact, as they will be limited by diffusion rate through a solid film. Only the relatively small amount of antiseptic will be capable of reaching the skin under usage conditions. With regard to the nature of specific antiseptics, for example, and without limitation, such ingredients include benzalkonium chloride, benzethonium chloride, chlorhexidine gluconate, chloroxylenol, hexylresorcinol, mercufenol chloride, methylbenzethonium chloride, secondary amyltricresols, sodium oxychlorosene, triclocarban, triclosan, hexachlorophene and tribromsalan.

Preferred antiseptic ingredients in embodiments intended for skin contact include, without limitation, those which are approved for use as food handler antiseptics, consumer antiseptics, and health care antiseptics. Suitable concentrations of antiseptics vary depending on the specific chemical species; however, benzalkonium chloride is known to be effective at around 100 ppm in aqueous media. Benzethonium chloride is known to be effective between 100-500 ppm. Chlorhexidine gluconate is known to be effective between 100-4000 ppm. Chloroxylenol is known to be effective around 5%. Effective concentrations of each of the antiseptics named herein are known to the skilled artisan or can be determined readily and without undue experimentation.

Emulsion embodiments may optionally include one or more fragrances, colorants, and/or bittering agents. For example, limonene, vanillin, or an essential oil as described herein may be included in an embodiment to confer an appealing scent to an embodiment.

Bittering agents such as denatonium benzoate (Bitrex®) may be added to guard against accidental ingestion. An effective amount of denatonium benzoate is known as low as 30-50 ppm.

Any of a variety of known colorants approved for skin contact may be added in an effective amount to embodiments, for instance, to color-code products or to color-match skin. As used here, an effective amount of a colorant is that which produces a desired coloration, without degrading emulsion stability or film performance as previously described herein. A specific amount of a colorant constituting an effective amount is readily ascertainable by the person having ordinary skill in the art without undue experimentation. Suitable colorants for embodiments intended for skin contact may be selected from 21 CFR Part 73 Subpart C-Cosmetics, 21 CFR Part 74 Subpart C-Cosmetics, and 21 CFR Part 82 Subparts B, C, and D. More specifically, colorants may include aluminum powder, annatto, bismuth citrate, bismuth oxychloride, bronze powder, caramel, carmine, β-carotene, chromium, hydroxide green, chromium oxide greens, copper powder, dihydroxyacetone, disodium, EDTA-copper, ferric ammonium, ferrocyanide, ferric ferrocyanide, guaiazulene, guanine, henna, iron oxides, lead acetate, luminescent, zinc sulfide, manganese violet, mica, potassium sodium, copper chlorophyllin (chlorophyllin-copper complex), pyrophyllite, silver, titanium dioxide, ultramarines, zinc oxide, D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C, Yellow No. 7, D&C Yellow No. 8, D&C Yellow No. 10, and D&C Yellow No. 11.

Color coding may be advantageous to discern one product grade from another. For instance, embodiments capable of protecting the skin from viral contaminants may be a different color than products only capable of functioning as a barrier to soiling. A hospital grade product may be colored differently from a consumer grade product. Alternatively, it may be desirable to color-match skin to promote discreetness.

Having thus described the invention, it is now claimed:
We claim:
1. An emulsion comprising:
(i) a bimodal acrylic random copolymer comprising polymeric subunits consisting of:
a first polymeric subunit, present between 1 to 5 wt %+/−0.5 wt %;
a second polymeric subunit, present between 21 to 41 wt %+/−0.1 wt %;
a third polymeric subunit, present between 27 to 57.5 wt %+/−0.1 wt %; and
a fourth polymeric subunit, present between 19 to 34 wt %+/−0.1 wt %, wherein the acrylic random copolymer is present in the emulsion between 40 to 55 wt %;
- (ii) water, wherein the water is present in the emulsion between 44 to 59 wt %;
- (iii) a buffer present in an amount effective to maintain a pH between 4 and 10; and
- (iv) a non-ionic surfactant present between 0.1 and 1.0 wt %.

2. The emulsion of claim 1, wherein the buffer is selected from one or more of bicarbonate; phosphate; citrate; glycine; borate; 2-amino-2-methyl-1,3-propanediol; N,N-bis(2-hydroxyethyl)taurine; 4-(2-hydroxyethyl)-1-piperizine ethanesulfonic acid; imidazole; 3-morpholinopropane-1-sulfonic acid; 3-{[1,3-dihydroxy-2-(hydroxymethyl)propan-2-yl]aminol}propane-1-sulfonic acid; or 2[[1,3-dihydroxy-2-(hydroxymethyl)propan-2-yl]amino]ethanesulfonic acid; and N-(2-hydroxy-1,1-bis (hydroxymethyl)ethyl)glycine.

3. The emulsion of claim 1, wherein the non-ionic surfactant is a 1,4-aryl comprising an aliphatic substituent between C5 and C16 and a polyethylene oxide substituent chain between 4 and 20 polyethylene oxide units long.

4. The emulsion of claim 3, wherein the aliphatic substituent comprises between C7 and C10, and the polyethylene oxide substituent chain is between 6 and 10 polyethylene oxide units long.

5. The emulsion of claim 3, wherein the polyethylene oxide substituent chain is from 9 to 10 polyethylene oxide units long.

6. The emulsion of claim 1, further comprising an effective amount of an antiseptic preservative.

7. The emulsion of claim 6, wherein the antiseptic preservative is selected from the group consisting of benzalkonium chloride, benzethonium chloride, chlorhexidine gluconate, chloroxylenol, hexylresorcinol, mercufenol chloride, methylbenzethonium chloride, secondary amyltricresols, sodium oxychlorosene, triclocarban, triclosan, hexachlorophene and tribromsalan.

8. The emulsion of claim 1, further comprising an additive selected from the group consisting of aloe, an essential oil, mineral oil, petrolatum, lanolin, dimethicone, hyaluronic acid, or glycerin.

9. The emulsion of claim 1, further comprising limonene, vanillin, or an essential oil.

10. The emulsion of claim 1, further comprising an effective amount of denatonium benzoate as a bittering agent.

11. The emulsion of claim 1, further comprising an effective amount of a colorant.

* * * * *